(12) United States Patent
Tschirren et al.

(10) Patent No.: US 10,569,025 B2
(45) Date of Patent: Feb. 25, 2020

(54) INJECTION DEVICE FOR ADMINISTERING A LIQUID PRODUCT

(71) Applicant: TecPharma Licensing AG, Burgdorf (CH)

(72) Inventors: Markus Tschirren, Burgdorf (CH); Juerg Hirschel, Bern (CH)

(73) Assignee: TecPharma Licensing AG, Burgdorf (CH)

( * ) Notice: Subject to any disclaimer, the term of this patent is extended or adjusted under 35 U.S.C. 154(b) by 727 days.

(21) Appl. No.: 15/246,858

(22) Filed: Aug. 25, 2016

(65) Prior Publication Data

US 2016/0361498 A1 Dec. 15, 2016

Related U.S. Application Data

(63) Continuation of application No. PCT/CH2015/000005, filed on Jan. 21, 2015.

(30) Foreign Application Priority Data

Feb. 26, 2014 (CH) .......................... 275/14

(51) Int. Cl.
*A61M 5/315* (2006.01)
*A61M 5/24* (2006.01)
*A61M 5/31* (2006.01)

(52) U.S. Cl.
CPC .......... *A61M 5/31541* (2013.01); *A61M 5/24* (2013.01); *A61M 5/31536* (2013.01);
(Continued)

(58) Field of Classification Search
CPC ................ A61M 5/24; A61M 5/31528; A61M 5/31526; A61M 5/31536; A61M 5/31541;
(Continued)

(56) References Cited

U.S. PATENT DOCUMENTS

2008/0071227 A1* 3/2008 Moser ............... A61M 5/31553
604/207
2008/0183139 A1* 7/2008 Burren ............. A61M 5/31553
604/211

(Continued)

FOREIGN PATENT DOCUMENTS

DE 102007026556 12/2008
EP 2351591 8/2011
(Continued)

OTHER PUBLICATIONS

International Preliminary Report on Patentability for PCT Patent Application No. PCT/CH2015/000005, dated Aug. 30, 2016.
(Continued)

*Primary Examiner* — William R Carpenter
*Assistant Examiner* — Larry R. Wilson
(74) *Attorney, Agent, or Firm* — Dorsey & Whitney LLP (57) ABSTRACT

An injection device for dosing and for releasing a defined dose of a liquid product includes: a threaded rod with a thread that includes teeth; a rotating sleeve with an engaging element that can engage with the teeth of the threaded rod; a guide sleeve having an engaging element that can engage with the teeth of the threaded rod; and a dosing sleeve arranged in an axially moveable manner in relation to the rotating sleeve and the guide sleeve, the dosing sleeve in a threaded engagement with the rotating sleeve.

19 Claims, 7 Drawing Sheets

(52) U.S. Cl.
CPC .... *A61M 5/31555* (2013.01); *A61M 5/31585* (2013.01); *A61M 2005/2407* (2013.01); *A61M 2005/2492* (2013.01); *A61M 2005/3125* (2013.01); *A61M 2005/3126* (2013.01)

(58) Field of Classification Search
CPC .......... A61M 5/31555; A61M 5/31585; A61M 2005/2407; A61M 2005/2492; A61M 2005/3125; A61M 2005/3126; A61M 2205/43; A61M 2205/44; A61M 2205/58–584
See application file for complete search history.

(56) References Cited

U.S. PATENT DOCUMENTS

| | | | |
|---|---|---|---|
| 2010/0094205 A1* | 4/2010 | Boyd | A61M 5/31595 604/68 |
| 2012/0095413 A1 | 4/2012 | Nzike et al. | |
| 2012/0136317 A1 | 5/2012 | Teucher et al. | |
| 2012/0296286 A1 | 11/2012 | Raab et al. | |
| 2012/0310168 A1 | 12/2012 | Plumptre et al. | |
| 2013/0110054 A1 | 5/2013 | Raab et al. | |
| 2013/0138051 A1 | 5/2013 | Smith et al. | |

FOREIGN PATENT DOCUMENTS

| | | |
|---|---|---|
| WO | WO 2006125329 | 11/2006 |
| WO | WO 2008019517 | 2/2008 |
| WO | WO 2013/007769 A1 | 1/2013 |
| WO | WO 2013178602 | 12/2013 |

OTHER PUBLICATIONS

International Search Report for PCT Patent Application No. PCT/CH2015/000005, dated Mar. 23, 2015.

* cited by examiner

INJECTION DEVICE FOR ADMINISTERING A LIQUID PRODUCT

CROSS-REFERENCE TO RELATED APPLICATIONS

This application is a Continuation of International Patent Application No. PCT/CH2015/000005 filed Jan. 21, 2015, which claims priority to Swiss Patent Application No. 275/14 filed Feb. 26, 2014, the entire contents of each are incorporated herein by reference for any and all purposes.

BACKGROUND

The present invention relates to an injection device for administering a liquid product, in particular a medicament such as, for example, teriparatide for osteoporosis therapy.

The term "medicament" here comprises any free-flowing medicinal formulation that is suitable for controlled administration through a means such as, for example, a cannula or hollow needle, comprising, for example, a liquid, a solution, a gel or a fine suspension, which contains one or more medicinal active substances. A medicament can be a composition with a single active ingredient or a premixed or co-formulated composition with several active ingredients from a single container. Medicaments include drugs such as peptides (for example, insulin, insulin containing medicaments, GLP-1 containing as well as derived or analogous preparations), proteins and hormones, biologically obtained or biologically active ingredients, active ingredients based on hormones or genes, nutrient formulations, enzymes, vaccines, DNA or RNA or oligonucleotides, antibodies or parts of antibodies as well as suitable base, auxiliary and carrier substances.

From WO2006/125329A1, a dosing device of an injection apparatus is known, by means of which a dose to be dispensed can be set variably. The dosing device comprises a rotating sleeve, which can be unscrewed from the dosing device for preparing a dose delivery in relation to a housing of the injection device.

From WO2008/019517A1, a defined dose injection apparatus is known, wherein a dose to be dispensed can be set simply by rotating the dosing button.

SUMMARY

A problem of the present invention is to provide an alternative injection device for dosing and for releasing a defined dose of a liquid product, or several defined doses, that is to say a first, second and additional doses until the last defined dose, wherein the defined doses are of equal size.

This problem is solved by the subject matter of the independent claim. Advantageous embodiments result from the dependent claims.

Herein, distal is understood to mean a direction towards the injection needle-side end of the injection device and proximal is understood to mean a direction towards the dosing button-side end.

The invention relates to an injection device for dosing and for releasing a defined dose of a liquid product with a threaded rod, wherein the thread has teeth. Furthermore, the injection device comprises a rotating sleeve and a guide sleeve, wherein the rotating sleeve and the guide sleeve each comprise an engaging element, which can engage in the teeth of the threaded rod. Multiple engaging elements can also be arranged on the rotating sleeve and on the guide sleeve and engage in the teeth of the threaded rod. The dosing sleeve can be in a threaded engagement with a rotating sleeve. Preferably, the threaded engagement is configured as a non-self-inhibiting (self-locking) thread connection. Furthermore, the rotating sleeve and the guide sleeve may be arranged so that they are axially fixed and rotatable in relation to one another. In addition, the rotating sleeve may be arranged so that it is rotatable in relation to the guide sleeve and/or to the dosing sleeve and/or threaded rod.

In order to set a defined dose of the liquid product, the rotating sleeve may be rotated in relation to the guide sleeve, until the rotation movement is limited by a first abutment contact between the rotating sleeve and the guide sleeve. For this purpose, the rotating sleeve may be rotated in a first rotation direction. For the dosing of the liquid product, the dosing sleeve may be pulled axially out of the injection device, while the dosing device can be axially pushed into the injection device for the administration of the liquid product. Therefore, for the administration of the liquid product, the rotating sleeve may be rotated in a second rotation direction, until the rotation movement is limited by a second abutment contact between the rotating sleeve and the guide sleeve. The first and the second abutment contacts between the rotating sleeve and the guide sleeve may be formed so that the rotating sleeve comprises a radially outward protruding protrusion, which can be moved by rotation back and forth between two radially inward protruding protrusions provided on the guide sleeve. Alternatively, the rotating sleeve comprises two outward protruding protrusions, which can be moved by rotation back and forth between corresponding radially inward protruding protrusions that are arranged on the guide sleeve.

The engaging element of the rotating sleeve and the engaging element of the guide sleeve can interact with the teeth of the threaded rod in such a manner that a rotation of the threaded rod is enabled in a rotation direction and blocked in the opposite rotation direction. For the administration of the liquid product from the injection device, the rotation of the threaded rod is enabled, while it is blocked for the dosing of the product. The threaded rod can be connected by means of the threaded connection to the guide sleeve or alternatively to a housing of the injection device. The guide sleeve can be connected in an axially fixed and rotationally fixed manner to the housing or alternatively it can be designed to form a single piece with the housing.

The engaging elements of the rotating sleeve and of the guide sleeve may be designed as resilient spring arms, wherein the engaging elements can be placed in the peripheral direction on the corresponding sleeves. The engaging elements of the rotating sleeve and of the guide sleeve can have a head with a steep flank and a flat flank. The heads may engage resiliently by means of spring arms in the teeth of the threaded rod. The engaging mechanism of the engaging elements of the rotating sleeve and of the guide sleeve into the teeth of the threaded rod may be configured as a ratcheting mechanism. For this purpose, the threaded rod can comprise several longitudinal notches or longitudinal grooves in the longitudinal direction, which form at least one tooth, preferably several teeth with one or more tooth gaps. The longitudinal notch or longitudinal groove or tooth gap has a steep and a flat surface.

The defined dose may be defined, on the one hand, by the rotation positions, which are defined between the first and second abutment contacts between the abutments of the rotating sleeve and the guide sleeve, and, on the other hand, by the thread pitch between the rotating sleeve and the dosing sleeve, or the axial path of the dosing sleeve. Alternatively or additionally, the axial path of the dosing sleeve may be limited by the axial abutments and counter-abutments. For this purpose, the dosing sleeve can comprise two axially spaced abutments.

The injection device may provide for a multiplication or a reduction of the speed of the pulling up movement of the dosing sleeve, or of the release movement of the threaded rod. For this purpose, the thread pitch of the threaded engagement between the guide sleeve or the housing and the threaded rod, and the thread pitch of the threaded engagement between the dosing sleeve and the rotating sleeve can be different. Preferably, the thread pitch of the threaded engagement between the dosing sleeve and the rotating sleeve is greater than the thread pitch of the threaded engagement between the guide sleeve or the housing and the threaded rod. Alternatively, the thread pitch of the threaded engagement between the guide sleeve or the housing and the threaded rod can be greater than or equal to the thread pitch of the threaded engagement between the dosing sleeve and the rotating sleeve.

Preferably, the rotating sleeve and the guide sleeve each have an engaging element, and the threaded rod has four longitudinal notches or longitudinal grooves or four longitudinal teeth with four tooth gaps, which are arranged with mutual offset in the peripheral direction by approximately 90 degrees. Alternatively, the rotating sleeve comprises two engaging elements, which are arranged on the rotating sleeve with mutual offset in the peripheral direction by approximately 180 degrees, and the guide sleeve comprises two engaging elements that are also arranged with mutual offset in the peripheral direction by approximately 180 degrees. Alternatively, in each case, four engaging elements may be provided on the rotating sleeve or guide sleeve, which are mutually offset in the peripheral direction by approximately 90 degrees.

Alternatively, the same number of engaging elements may be provided on the rotating sleeve and on the guide sleeve as the number of longitudinal notches or longitudinal grooves of the threaded rod or the number of longitudinal teeth or tooth gaps of the threaded rod.

Preferably, the injection device comprises two abutment contacts arranged with mutual offset in the peripheral direction between the rotating sleeve and the guide sleeve, wherein the distance between the two abutments corresponds approximately to the distance between two adjacent engagement positions of the engaging element of the rotating sleeve and/or of the guide sleeve in the longitudinal notch or longitudinal groove or tooth gap of the threaded rod.

The engaging elements of the rotating sleeve and of the guide sleeve, and the teeth of the threaded rod can be designed so that, during the dosing and during the release of the liquid product, one or more click sounds can be generated.

Due to the thread connection between the dosing sleeve, which can be mounted in the housing of the injection device, and the rotating sleeve, which can be provided in an axially moveable and rotatable manner in the housing of the injection device, the rotating sleeve, during the dosing and during the release of the liquid product, can in each case reach a rotation direction in dosing and release direction.

During the dosing of the liquid product, the threaded rod may be held in an axially fixed and rotationally fixed manner by means of the engagement between the engaging element of the guide sleeve and the teeth of the threaded rod in relation to the housing of the injection device. For this purpose, a steep flank of the head of the engaging element of the guide sleeve and a steep flank of the longitudinal notch or longitudinal groove or tooth or tooth gap come in abutment contact. Furthermore, during the dosing of the liquid product, the engaging element of the rotating sleeve can become disengaged from the teeth of the threaded rod. In the process, a flat flank of the head of the engaging element of the rotating sleeve slides over a flat flank of the longitudinal notch or of the longitudinal groove or tooth or tooth gap of the threaded rod, and reaches the next longitudinal notch or longitudinal groove or tooth gap of the threaded rod.

During the release of the liquid product, the rotating sleeve can transmit the rotation movement to the threaded rod, due to an abutment between a steep flank of the head of the engaging element of the rotating sleeve and a steep flank of the longitudinal notch or of the longitudinal groove or tooth of the threaded rod. In the process, a flat flank of the head of the engaging element of the guide sleeve slides over a flat flank of the longitudinal notch or longitudinal groove or tooth or tooth gap of the threaded rod. During the release of the defined dose, due to the thread connection between the threaded rod and the guide sleeve or alternatively the housing, the threaded rod can be screwed in the distal direction. In the process, the engaging element, in particular, the head or a part of the head of the rotating sleeve slides axially along the longitudinal notch or longitudinal groove of the threaded rod. The threaded rod moves axially in relation to the housing of the injection device in the distal direction and, via a flange, it pushes a plug in the distal direction. The flange can be attached in an axially fixed manner and preferably rotatably on the distal end of the threaded rod. The plug in a cartridge can push the liquid product out via an injection needle attached on the cartridge or on a cartridge holder receiving the cartridge.

For the protection of the cartridge or of the cartridge holder receiving the cartridge, the injection device can comprise a closing cap. The closing cap can be connected in an axially fixed and preferably rotatable manner to the housing of the injection device. The closing cap can be removed from the injection device, in order to install, before the use of the injection device, an injection needle on the cartridge, in that a cannula of the injection needle can perforate a septum of the cartridge, in order to form a fluidic connection between the injection needle and the cartridge.

The injection device can provide a dosing button, which may be connected in an axially fixed and preferably rotationally fixed manner to the proximal end of the dosing sleeve. The dosing button may form a single piece with the dosing sleeve.

In addition, the injection device can provide a mechanism that can prevent a setting of an additional dose, when the last dose has been released.

For this purpose, the rotating sleeve of the injection device can comprise an abutment, which abuts against an abutment provided on the threaded rod. In this way, due to an axial and/or radial abutment contact between the rotating sleeve and the threaded rod, the setting or pulling up of an additional dose can be prevented, when the last dose has been released. Preferably, two abutments can be provided on the rotating sleeve, which can come in abutting contact with two corresponding abutments provided on the threaded rod, and in this way prevent a rotation movement of the rotating sleeve in the dosing direction.

In an embodiment example, the dosing sleeve can be arranged between the rotating sleeve and the guide sleeve. In another embodiment, the guide sleeve and the dosing sleeve can be arranged coaxially in the injection device. The thread connection between the rotating sleeve and the dosing sleeve can be designed as a single pitch or multiple pitch thread connection or as segments of a thread connection.

Furthermore, the injection device can comprise an indicator device, which can indicate the start position, the pulled up position and/or the released position of the dosing sleeve or of the setting button. The indicator device can be formed as a visual, acoustic and/or tactile indicator. The visual indicator device can comprise a marking and/or a symbol and/or an indicator number.

For this purpose, the injection device can comprise an indicator sleeve with an indicator device. Preferably, the indicator sleeve is connected to the dosing sleeve so as to form a single piece. Alternatively, the dosing sleeve can comprise an indicator device. Furthermore, the dosing sleeve can comprise a visual indicator device in the form of print and/or an adhesive label.

BRIEF DESCRIPTION OF THE DRAWINGS

FIG. 2b is the injection device shown in FIG. 2a in a cross-sectional view, wherein the cross-sectional view corresponds to the cross-sectional line A-A drawn in FIG. 2a.

FIG. 2c is the injection device shown in FIG. 2a in cross-sectional view, wherein the cross-sectional view corresponds to the cross-sectional line B-B drawn in FIG. 2a.

FIG. 2d shows a portion of device just to the left of the cross section line B-B in FIG. 2a.

FIG. 3b is the injection device shown in FIG. 3a in a cross-sectional view, wherein the cross-sectional view corresponds to the cross-sectional line C-C drawn in FIG. 2a.

FIG. 3c is the injection device shown in FIG. 3a in a cross-sectional view, wherein the cross-sectional view corresponds to the cross-sectional line D-D drawn in FIG. 2a.

DETAILED DESCRIPTION

Figure 1:
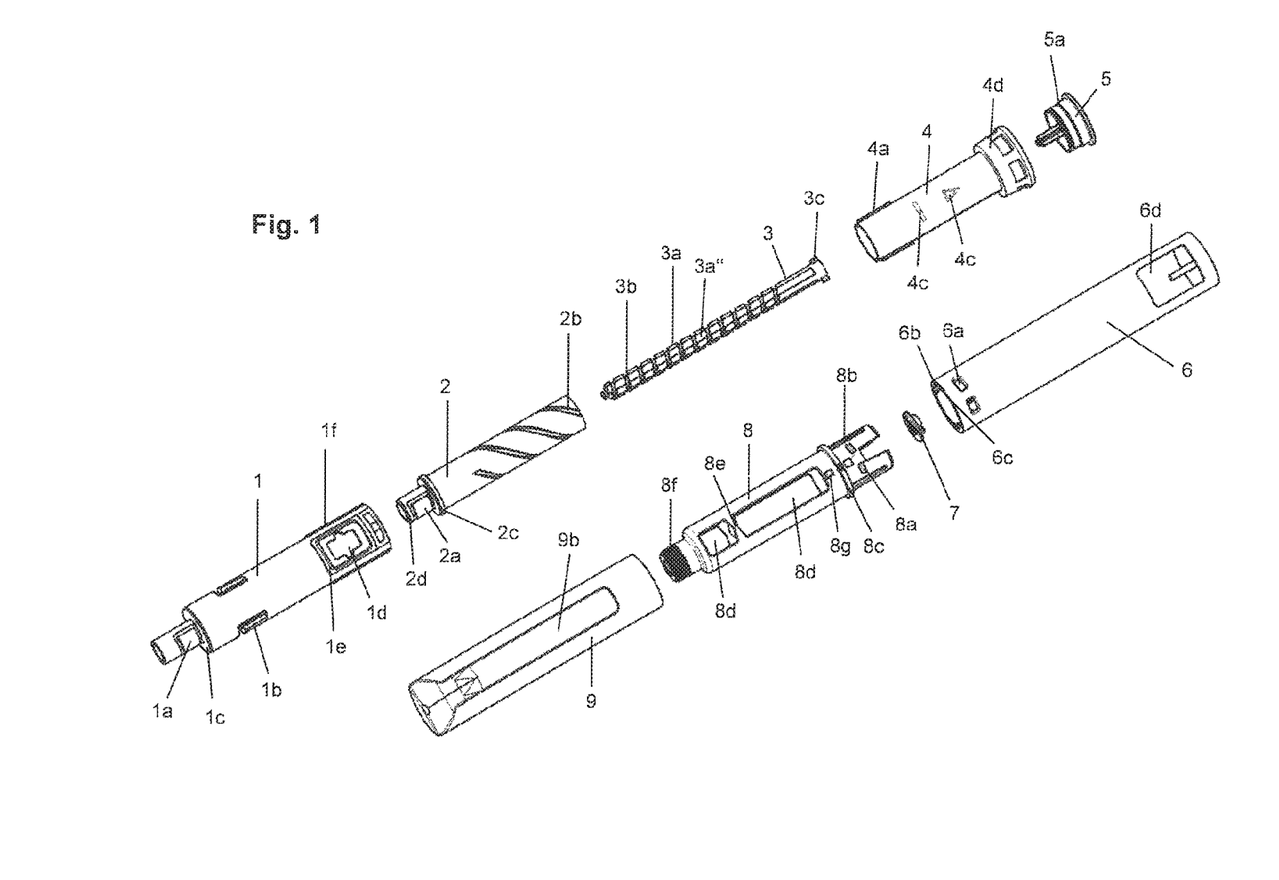
FIG. 1 is an exploded view of a first embodiment of an injection device.

In FIG. 1, an exploded view of a first embodiment of an injection device according to the invention is represented.

Figure 2A:
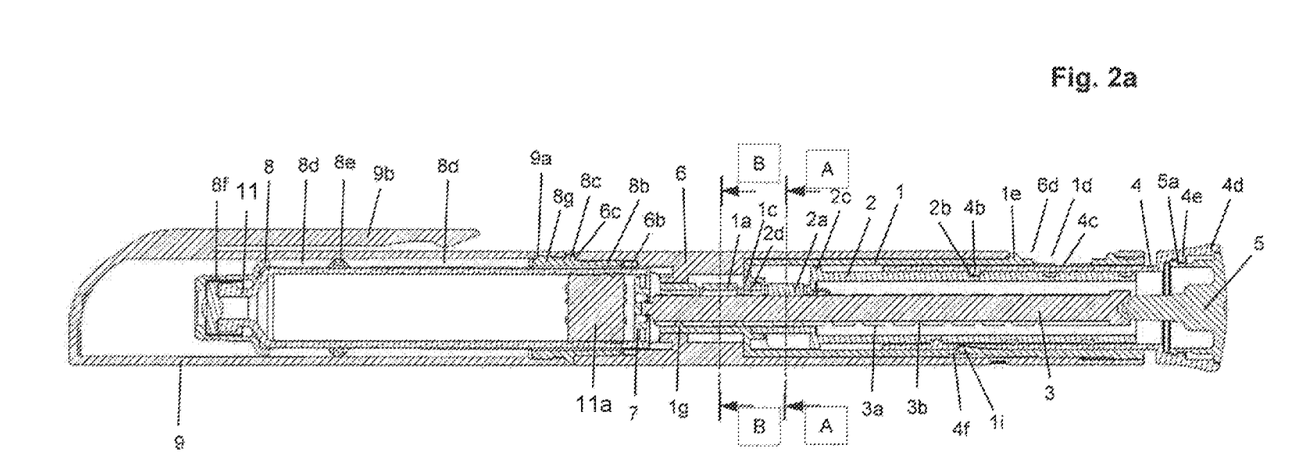
FIG. 2a is a longitudinal cross-sectional view of the first embodiment of the injection device in a start position of a dosing sleeve.

The injection device comprises a cartridge holder (8), which can receive a cartridge (for example, in FIG. 2a; 11), wherein the cartridge holder (8) is connected in an axially fixed manner via a cartridge holder nose (8a) to a distal housing nose recess (6a) of a housing (6). Furthermore, on the cartridge holder (8), a cartridge holder web (8b) is provided for the rotationally fixed connection via a corresponding housing groove (6b) to the housing (6). A cartridge holder abutment (8c) can abut axially against a distal housing edge (6c) of the housing (6). A cartridge holder recess (8d) in the cartridge holder (8) is used for indicating the relative position of a plug (for example, in FIG. 2a; 11a) that is axially movable in the cartridge (for example, in FIG. 2a; 10). The cartridge holder recess (8d) is interrupted by a cartridge holder transverse web (8e), wherein the cartridge holder recess (8d) is divided into two parts. If the plug (for example, in FIG. 4a; 11a) is in the more distally arranged portion of the cartridge holder recess (8d), the user obtains, for example, the information that the last dose has been released from the injection device and that no new dose can be pulled up. On the distal end of the cartridge holder (8), a needle connection element (8f) is provided, which is provided for the detachable attachment of an injection needle (not visible). The injection device moreover comprises a closing cap (9), which can be connected via a detachable connection to the cartridge holder (8). For this purpose, the cartridge holder (8) comprises a cartridge holder protrusion (8g), which can engage in an annular groove (for example, in FIG. 2a; 9a) of the closing cap (9). The closing cap (9) can preferably comprise a closing cap clip (9b). Preferably, the annular groove (for example, in FIG. 2a; 9a) of the closing cap (9) comprises an indentation, so that the closing cap (9) can be arranged in a rotationally fixed manner in relation to the cartridge holder (8). Furthermore, the injection device comprises a guide sleeve (1), which is connected in an axially fixed and rotationally fixed manner to the housing (6) of the injection device by a positive-locking connection. For this purpose, the housing (6) comprises a housing window (6d), which receives a guide sleeve window frame (1e) protruding radially outward, around a guide sleeve window (1d). Furthermore, on the guide sleeve (1), a guide sleeve web (10 is arranged, which, together with a groove (not visible) forms a rotationally fixed connection in the housing (6). The guide sleeve (1) comprises an engaging element (1a), which can cooperate with the teeth of the threaded rod (3). (In an alternative embodiment, as seen in a detail view in FIG. 2d, the housing (6) comprises an engaging element in the form of an extension (6e) at the distal end of housing (6), forming a threaded connection between the threaded rod (3) and the housing (6). This alternative can replace the guide sleeve (1) engaging element (1a) in a threaded connection with the threaded rod (3), as seen in FIG. 2a.) The injection device moreover comprises a rotating sleeve (2), which is connected in an axially fixed and rotatable manner to the guide sleeve (1). For this purpose, the rotating sleeve (2) comprises a rotating sleeve annular projection (2c), which can abut axially against the guide sleeve holding arm (1b), preferably at two guide sleeve holding arms (1b), wherein, furthermore, the rotating sleeve edge (2d) can form an axial abutment contact with the guide sleeve front side (1c) of the guide sleeve (1). The rotating sleeve (2) also comprises an engaging element (2a), which can cooperate with the teeth of the threaded rod (3). The teeth of the threaded rod (3) comprises a tooth (3a), preferably several teeth, particularly preferably four teeth. Furthermore, the threaded rod (3) comprises an outer thread (3b), which, together with an inner thread (for example, in FIG. 2a; 1g)

of the guide sleeve, forms a thread connection. The engaging mechanism of the engaging elements (2a; 1a) of the rotating sleeve (2) and of the guide sleeve (1) into the teeth of the threaded rod (3) is designed as a ratcheting mechanism. The engaging elements (2a, 1a) of the rotating sleeve (2) and of the guide sleeve (1) cooperate with the teeth of the threaded rod (3) in such a way that during the dosing of the defined dose and during the release of the defined dose, a click noise is generated. In order to prevent a setting of an additional dose when the last dose has been released, the rotating sleeve (2) comprises a rotating sleeve abutment (for example, in FIG. 4b; 2e), which can come in abutting contact with a threaded rod abutment (3c) provided on the threaded rod (3). The injection device moreover comprises a dosing sleeve (4). The dosing sleeve (4) is mounted in a rotationally fixed and axially moveable manner via a dosing sleeve web (4a) with a guide sleeve groove (not visible) of the guide sleeve (1) in relation to the housing (6) of the injection device. The user can move the dosing sleeve (4) axially back and forth by means of a dosing sleeve grip (4d) arranged on the proximal end of the dosing sleeve (4). For the indication of the individual dosing movements, the dosing sleeve (4) preferably comprises an indicator (4c). In addition, on the proximal end of the dosing sleeve (4), a dosing button (5) can be provided, which is connected in an axially fixed manner via a dosing button groove (5a), e.g., an annular groove, to a dosing sleeve annular projection (4e) of the dosing sleeve (4). The dosing sleeve (4) is connected via a thread connection to the rotating sleeve (2). The inner side of the dosing sleeve (4) comprises a dosing sleeve thread (for example, in FIG. 2a; 4b), which is in engagement with the rotating sleeve thread (2b) on the outer side of the rotating sleeve (2).

Figure 2B:
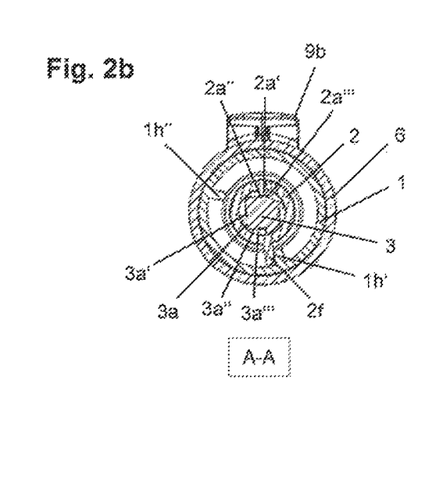
Figure 2C:
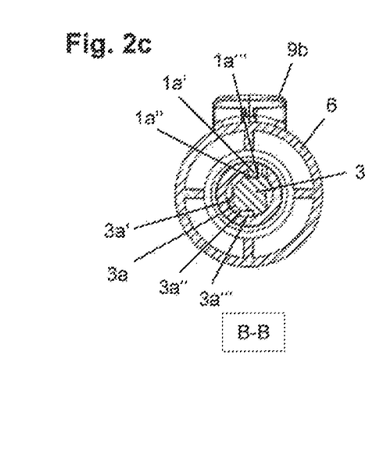
Figure 2D:
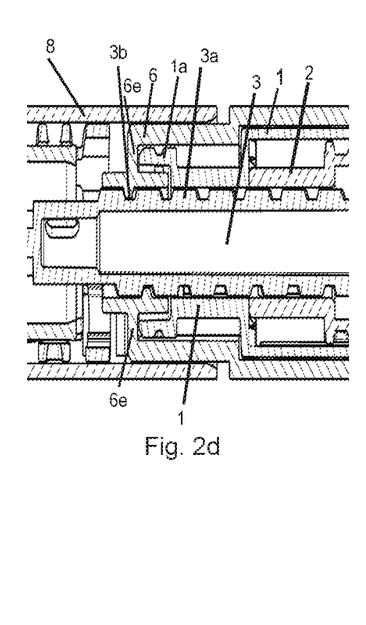
FIG. 2d is an enlarged detail view of a portion of a device similar to that seen in cross section in FIG. 2a that shows an alternative embodiment with the housing (instead of the guide sleeve) providing a threaded connection with the threaded rod.

In FIG. 2a, a longitudinal cross-sectional view of the first embodiment of the injection device in a start position of the dosing sleeve (4) is represented. The dosing sleeve (4), which is mounted in an axially moveable and rotationally fixed manner in the housing (6), is inserted into the injection apparatus, wherein the indicator (4c) placed on the dosing sleeve (4) can be seen through the guide sleeve window (1d) and through the housing window (6d), and indicates to the user that the injection device is in the start position. The dosing sleeve (4) is in a threaded engagement via the dosing sleeve thread (4b) and the rotating sleeve thread (2b) of the rotating sleeve (2). As can be seen in FIG. 2b, a radially outward protruding protrusion (2f) of the rotating sleeve (2) is in abutment contact with a radially inward protruding first protrusion (1h') of the guide sleeve (1). A head (2a'), which is placed on the engaging element (2a) of the rotating sleeve (2), is in engagement with the teeth of the threaded rod (3). For this purpose, the head (2a') of the engaging element (2a) of the rotating sleeve (2) engages between two adjacent teeth (3a) into a tooth gap (3a''') of the threaded rod (3), namely between a steep flank (3a') of a tooth (3a) and a flat flank (3a'') of an adjacent tooth (3a) of the threaded rod (3). Furthermore, as represented in FIG. 2c, a head (1a') provided on the engaging element (1a) of the guide sleeve (1) is also in engagement with the teeth of the threaded rod (3). For this purpose, the head (1a') of the engaging element (1a) of the guide sleeve (1) also engages between two adjacent teeth (3a) in a tooth gap (3a''') of the threaded rod (3). The head (1a') of the engaging element (1a) of the guide sleeve is located between a steep flank (3a') of a tooth (3a) and a flat flank (3a'') of an adjacent tooth (3a) of the threaded rod (3). For the relative position between the dosing sleeve (4) and the guide sleeve (1) to be defined, a radially inward prestressed guide sleeve catch (1i) of the guide sleeve (1) is in engagement with a dosing sleeve recess (4f) provided on the dosing sleeve (4). This engagement forms a frictional connection between the guide sleeve catch (1i) and the dosing sleeve recess (4f). Furthermore, this engagement can eliminate play between the dosing sleeve (4), the rotating sleeve (2), the threaded rod (3), and the guide sleeve (1).

Figure 3A:
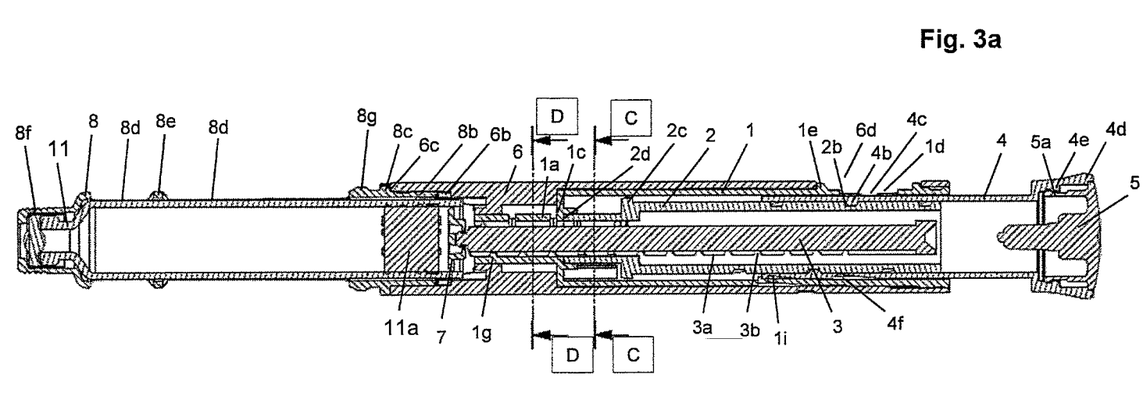
FIG. 3a is a longitudinal cross-sectional view of the first embodiment of the injection device in a pulled up position of the dosing sleeve.
Figure 3B:
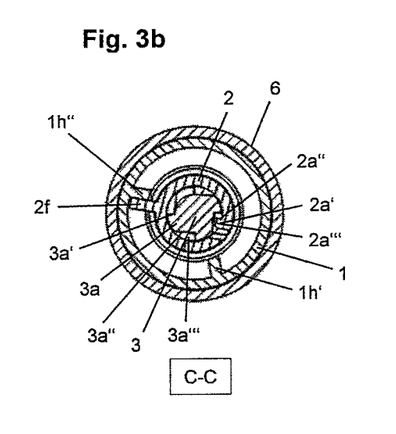
Figure 3C:
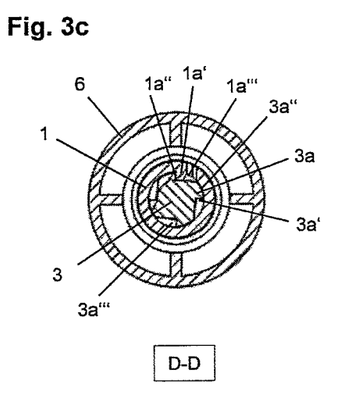

In FIG. 3a, a longitudinal cross-sectional view of the first embodiment of the injection device is shown in a pulled up position of the dosing sleeve (4). In order to set or pull up a dose, the user pulls the dosing sleeve grip (4d) in the proximal direction. In the process, the dosing sleeve (4) is moved axially in the proximal direction. The guide sleeve catch (1i) of the guide sleeve (1) slides out of engagement with the dosing sleeve recess (4f) of the dosing sleeve (4). Due to the threaded engagement between the dosing sleeve (4) and the rotating sleeve (2), the rotating sleeve (2) rotates in a first rotation direction until the protrusion (2f) of the rotating sleeve (2) comes in abutting contact with a second radially inward protruding protrusion (1h'') of the guide sleeve (1), as represented in FIG. 3b. In the process, the flat flank (2a''') of the head (2a') of the engaging element (2a) of the rotating sleeve (2) slides over the flat flank (3a'') of the tooth (3a) of the threaded rod (3) and in the process it arrives in an adjacent tooth gap (3a'''). As can be seen in FIG. 3c, the steep flank (1a'') of the head (1a') of the engaging element (1a) of the guide sleeve (1) is in abutment contact with the steep flank (3a') of the tooth (3a) of the threaded rod (3), so that the threaded rod (3) is held in a rotationally fixed manner. The indicator (4c) attached on the dosing sleeve (4) shows the user through the guide sleeve window (1d) and through the housing window (6d) that the injection device is in the pulled up position.

The pull up movement of the dosing sleeve (4) and the release movement of the threaded rod (3) may be transmitted in relation to the rotating sleeve (2) and the guide sleeve (1). The thread pitch of the thread connection (4b, 2b) between the dosing sleeve (4) and the rotating sleeve (2) is greater than the thread pitch of the thread connection (3b, 1g) between the threaded rod (3) and the guide sleeve (1).

In order to release a defined dose, the user presses the dosing button (5) in the distal direction, wherein the dosing sleeve (4) is shifted axially in the distal direction. The rotating sleeve (2) rotates in the rotation direction opposite the first rotation direction until the protrusion (2f) of the rotating sleeve (2) comes in abutting contact with the first radially inward protruding protrusion (1h') of the guide sleeve (1), as represented in FIG. 2b. The steep flank (2a'') of the head (2a') of the engaging element (2a) of the rotating sleeve (2) is in abutting contact with the steep flank (3a') of the tooth (3a) of the threaded rod (3) and transmits a torque to the threaded rod (3). As a result, due to the thread connection between the inner thread (1g) of the guide sleeve (1) and the outer thread (3b) of the threaded rod (3), the threaded rod (3) is screwed in the distal direction. In the process, the head (2a') of the engaging element (2a) of the rotating sleeve (2) slides axially along the tooth gap (3a''') of the threaded rod (3). The flat flank of the head (1a''') of the guide sleeve (1) slides over the flat flank of the tooth (3a'') of the threaded rod. In the process, via a flange (7) firmly attached axially on the threaded rod (3), a plug (11a) received by a cartridge (11) is pushed in the axial direction. The plug (11a) can press the liquid product via an injection needle (not visible) attached on the cartridge holder.

Figure 4A:
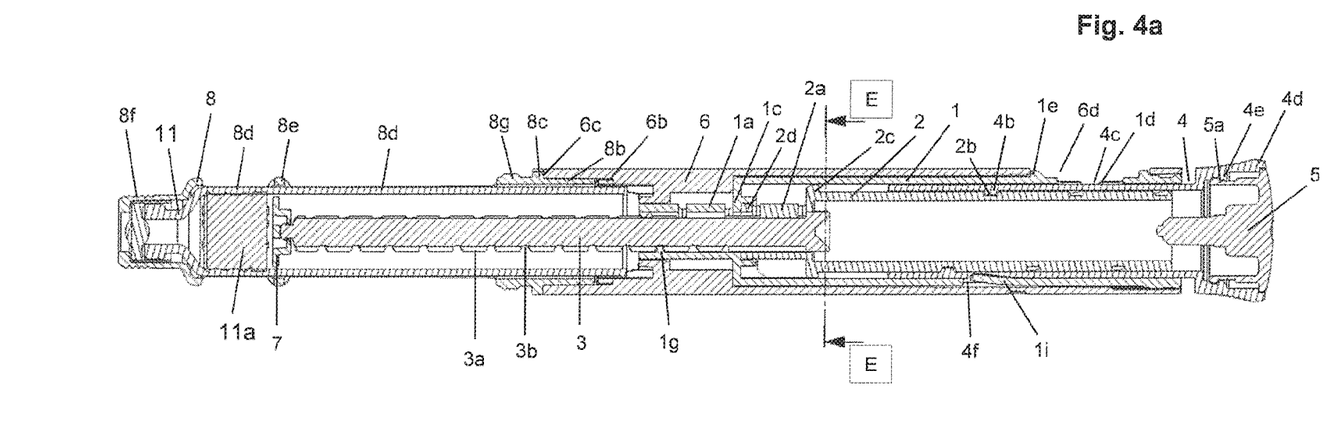
FIG. 4a is a longitudinal cross-sectional view of the first embodiment of the injection device after the release of the last dose.
Figure 4B:
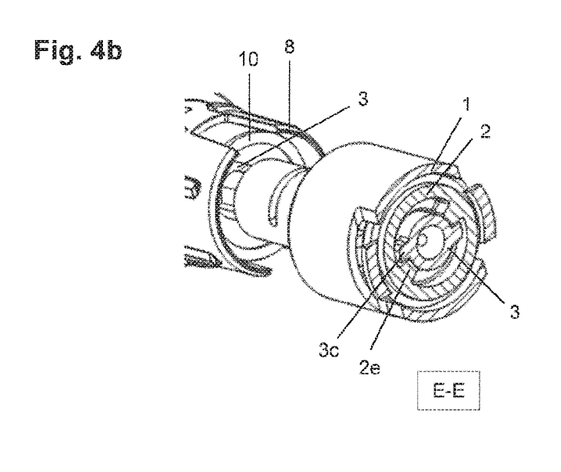
FIG. 4b is the injection device shown in FIG. 4a in a detail view, wherein the detail view corresponds to the cross-sectional line E-E drawn in FIG. 4a, wherein a portion of the housing is left out so in order to show the interior of the injection device.

In FIG. 4a, a longitudinal cross section of the first embodiment of the injection device after the release of the last dose is represented. After the last dose has been released from the injection device, the plug (11a) is in the distally arranged part of the cartridge holder recess (8*d*), which is divided into two parts by the cartridge transverse web (8*e*). The user thus obtains the information that the last dose has been released from the injection device and that no new dose can be pulled up. As shown in FIG. 4*b*, two rotating sleeve abutments (2*e*) of the rotating sleeve (2) are in abutting contact with the corresponding two threaded rod abutments (3*c*) of the threaded rod (3). Thus, no additional dose can be pulled up via the dosing sleeve (4), since a rotation of the rotating sleeve (2) is blocked.

Figure 5:
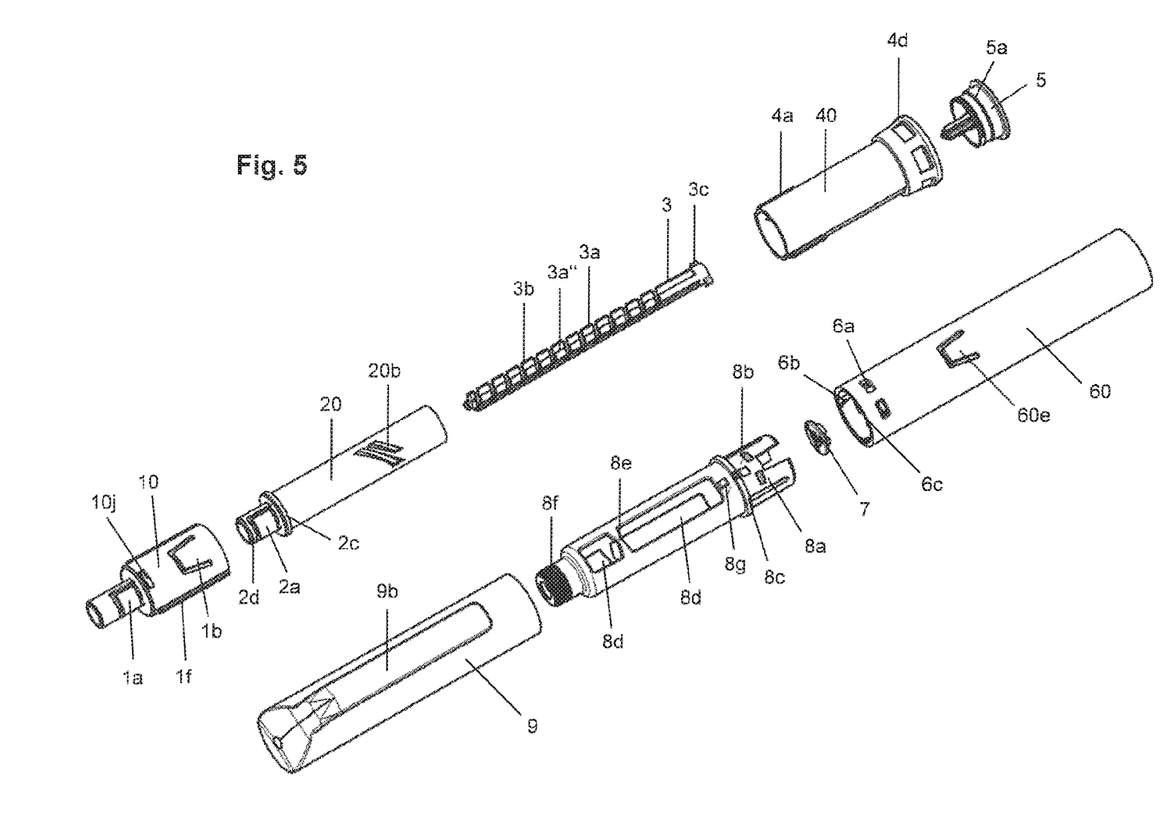
FIG. 5 is an exploded view of a second embodiment of an injection device.

In FIG. 5, an exploded view of a second embodiment of an injection device according to the invention is represented. The injection device differs from the injection device of the first embodiment substantially only with regard to the design of the guide sleeve (10), the dosing sleeve (40), the rotating sleeve (20), and the housing (60). The guide sleeve (10) is connected in a rotationally fixed manner to the housing (60) via a guide sleeve web (1*f*) provided on the guide sleeve (10) and via a groove (6*b*) provided on the housing (60), and it is connected in an axially fixed manner via an inward protruding guide sleeve protrusion (10*j*) of the guide sleeve (10) and via a housing holding arm (60*e*) attached on the housing (60). The rotating sleeve (20) comprises an outer thread, which is in thread connection with an inner thread of the dosing sleeve (40). The outer thread of the rotating sleeve (20) is configured as a rotating sleeve thread or as a rotating sleeve thread segment (20*b*), and the inner thread of the dosing sleeve (40) is designed as a dosing sleeve thread or as a dosing sleeve thread segment (40*b*). Furthermore, the guide sleeve (10) and the housing (60) have no window through which an indicator is visible. The dosing sleeve (40) can have no indicator or alternatively an indicator in the form of a marking, for example, in the form of a line (not visible), wherein the marking in a start position of the dosing sleeve (40) is covered by the housing (60) and visible in a pulled up position of the dosing sleeve (40). With regard to the interaction of the remaining parts of the second embodiment of the injection device according to the invention, reference is made to the injection device of the first embodiment according to FIG. 1 and its descriptions.

Figure 6A:
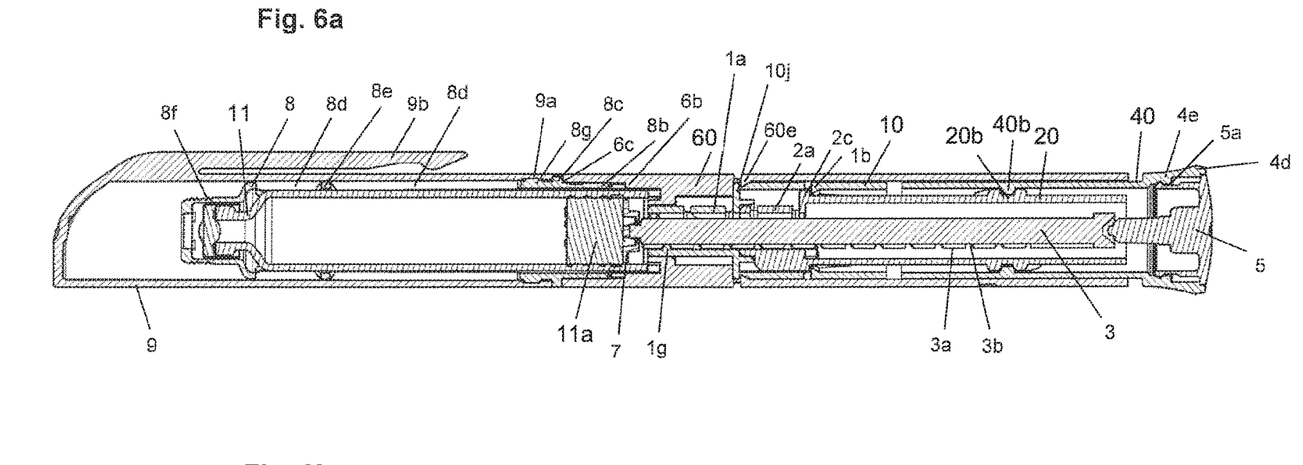
FIG. 6a is a longitudinal cross-sectional view of the second embodiment of the injection device in a start position of a dosing sleeve.
Figure 6B:
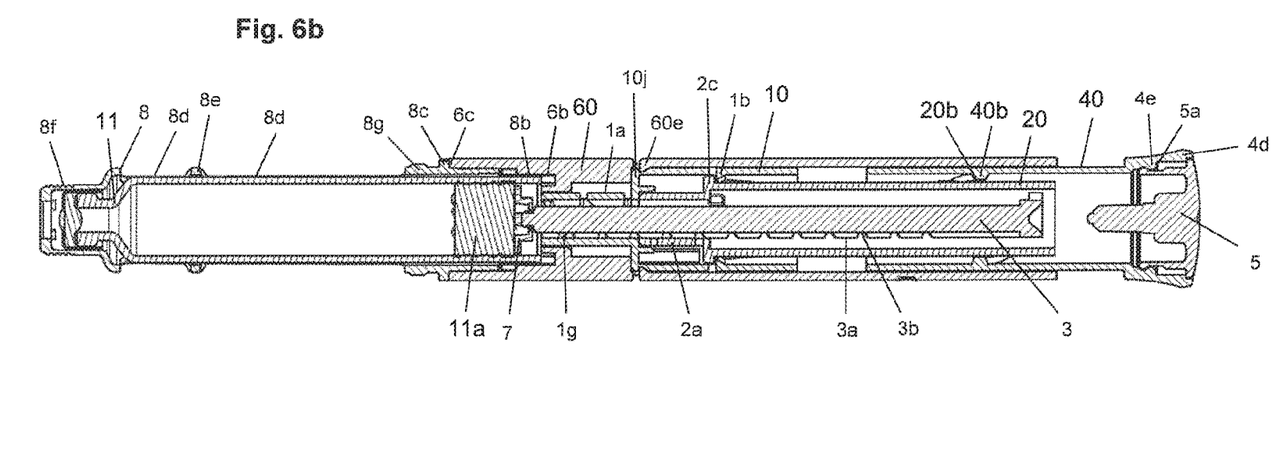
FIG. 6b is a longitudinal cross-sectional view of the second embodiment of the injection device in a pulled up position of the dosing sleeve.
Figure 6C:
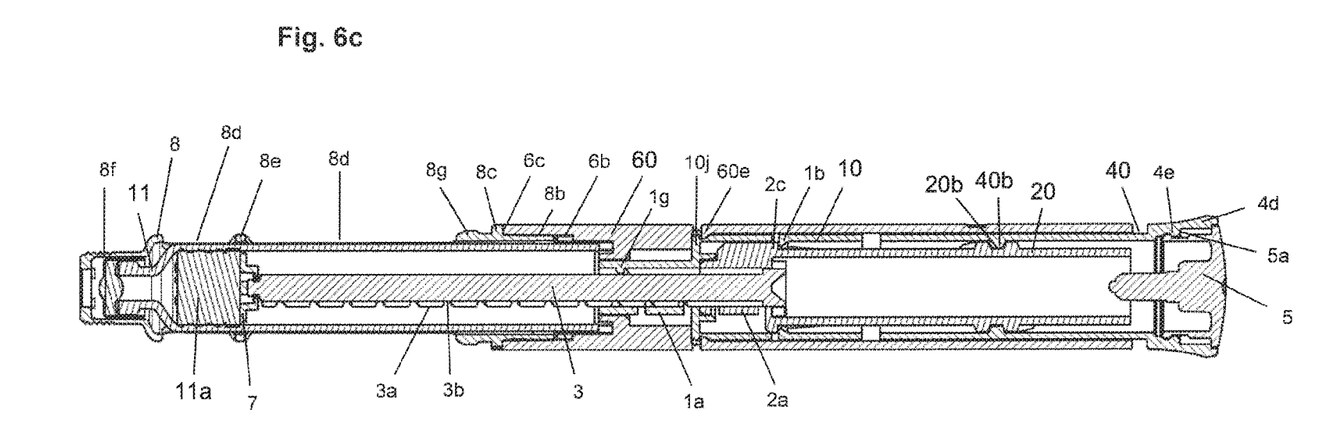
FIG. 6c is a longitudinal cross-sectional view of the second embodiment of the injection device after the release of the last dose.

In FIG. 6*a*, a longitudinal cross-sectional view of the second embodiment of the injection device is shown in a start position of a dosing sleeve (40), and in FIG. 6*b*, a longitudinal cross-sectional view of the second embodiment of the injection device is represented in a pulled up position of the dosing sleeve (40). Furthermore, FIG. 6*c* shows a longitudinal cross-sectional view of the second embodiment of the injection device after the release of the last dose. FIGS. 6*a*, 6*b* and 6*c* show the interaction of the guide sleeve (10), the rotating sleeve (20), the threaded rod (3) of the dosing sleeve (40), the dosing head (5), the housing (60), the flange (7), the cartridge holder (8), the closing cap (9), the cartridge (11) and the plug (11*a*) according to the first embodiment shown in FIGS. 2*a*, 2*b*, 2*c*, 3*a*, 3*b*, 3*c*, 4*a* and 4*b*. Thus, reference is made to the function description of the first embodiment according to the one shown in FIGS. 2*a*, 2*b*, 2*c*, 3*a*, 3*b*, 3*c*, 4*a* and 4*b* and their descriptions, which are to be applied to the second embodiment of the injection device except for the differences mentioned in FIG. 5.

The invention claimed is:

1. An injection device for dosing and for releasing a defined dose of a liquid product, comprising:
    a threaded rod comprising a thread, the thread comprising teeth;
    a rotating sleeve comprising an engaging element, wherein the engaging element of the rotating sleeve is configured to engage with the teeth of the threaded rod;
    a guide sleeve comprising an engaging element, wherein the engaging element of the guide sleeve is configured to engage with the teeth of the threaded rod; and
    a dosing sleeve configured to be axially moveable in relation to the rotating sleeve and the guide sleeve, wherein the dosing sleeve is in a threaded engagement with the rotating sleeve.

2. The injection device of claim 1, wherein the threaded rod is in a threaded connection with the guide sleeve or with a housing of the injection device.

3. The injection device of claim 2, wherein a thread pitch of the threaded connection between the guide sleeve or the housing and the threaded rod is different from a thread pitch of the threaded engagement between the dosing sleeve and the rotating sleeve.

4. The injection device of claim 3, wherein the thread pitch of the threaded engagement between the dosing sleeve and the rotating sleeve is greater than the thread pitch of the threaded connection between the guide sleeve or the housing and the threaded rod.

5. The injection device of claim 3, wherein the thread pitch of the threaded connection between the guide sleeve or the housing and the threaded rod is greater than or equal to the thread pitch of the threaded engagement between the dosing sleeve and the rotating sleeve.

6. The injection device of claim 1, wherein the rotating sleeve and the guide sleeve are arranged axially fixed in relation to one another.

7. The injection device of claim 1, wherein the rotating sleeve and the guide sleeve are rotatable relative to one another.

8. The injection device of claim 7, wherein a rotational movement between the rotating sleeve and the guide sleeve is limited by an abutment contact between the rotating sleeve and the guide sleeve.

9. The injection device of claim 1, wherein the rotating sleeve and the dosing sleeve are rotatable relative to one another.

10. The injection device of claim 1, wherein the rotating sleeve and the threaded rod are rotatable relative to one another.

11. The injection device of claim 10, wherein a rotational movement between the rotating sleeve and the threaded rod is limited by an abutment contact between the rotating sleeve and the threaded rod.

12. The injection device of claim 1, wherein the dosing sleeve is configured to be pulled axially out of the injection device for dosing the liquid product, and axially pushed into the injection device for an administration of the liquid product.

13. The injection device of claim 1, wherein an axial path of the dosing sleeve is limited by axial abutments and counter-abutments.

14. The injection device of claim 1, wherein the engaging element of the rotating sleeve and the engaging element of the guide sleeve interact with the teeth of the threaded rod such that a rotation of the threaded rod is enabled in a first rotational direction and is blocked in a second, opposite rotational direction.

15. The injection device of claim 1, wherein the dosing sleeve is arranged between the rotating sleeve and the guide sleeve.

16. An injection device for dosing and for releasing a defined dose of a liquid product, comprising:
    a threaded rod comprising a thread, the thread comprising teeth;

a rotating sleeve comprising an engaging element, wherein the engaging element of the rotating sleeve is configured to engage with the teeth of the threaded rod;

a guide sleeve comprising an engaging element, wherein the engaging element of the guide sleeve is configured to engage with the teeth of the threaded rod, wherein the teeth of the threaded rod engage with the engaging elements of the rotating sleeve and the guide sleeve such that the threaded rod rotates during release of the liquid product and is blocked from rotating during dosing of the product; and a dosing sleeve configured to be axially moveable in relation to the rotating sleeve and the guide sleeve, wherein the dosing sleeve is in a threaded engagement with the rotating sleeve.

17. The injection device of claim 16, wherein the threaded rod is in a threaded connection with the guide sleeve or with a housing of the injection device.

18. The injection device of claim 16, wherein during dosing of the product, the threaded rod is held in an axially and rotationally fixed manner by an engagement between the engaging element of the guide sleeve and the teeth of the threaded rod, and the engaging element of the rotating sleeve disengages from the teeth of the threaded rod.

19. The injection device of claim 16, wherein during release of the liquid product, the rotating sleeve rotates and transmits a rotational movement to the threaded rod such that the threaded rod is screwed in a distal direction and the engaging element of the rotating sleeve slides axially along the threaded rod.

* * * * *